United States Patent [19]

Starling et al.

[11] Patent Number: Plant 7,167

[45] Date of Patent: Feb. 27, 1990

[54] APPLE TREE-STARLING CULTIVAR

[76] Inventors: David Starling; Teresa Starling, both of R.R. #1, Oyama, British Columbia, Canada, V0H 1W0

[21] Appl. No.: 32,435

[22] Filed: Mar. 31, 1987

[51] Int. Cl.[4] ..... A01H 5/03

[52] U.S. Cl. ..... Plt./34

[58] Field of Search ..... Plt./34

*Primary Examiner*—Robert E. Bagwill

[57] ABSTRACT

This is a new and distinct apple tree, being a limb mutation of a McIntosh apple tree.

2 Drawing Sheets

DESCRIPTION

This distinct new apple cultivar was discovered as a limb mutation of a McIntosh tree in the early 1970's growing in the orchard of David and Teresa Starling, of Oyama, British Columbia, Canada. Fruit on this single branch developed a pronounced stripe weeks ahead of the other fruit on the tree and a full red color at maturity when compared to other typical McIntosh fruits on the remainder of the tree with only partial red color at maturity (FIG. 1). The Starling cultivar color development differs from Macspur (patented) cultivar in that it develops about 7 days earlier, and further it also starts to develop as a striped pattern as opposed to the solid blush pattern color characteristic of the Greenslade variety, U.S. Plant Pat. No. 2,982 (a/k/a/ Macspur R), Summerland cultivar and Imperial McIntosh cultivar. Comparing color development another way, the color on Starling cultivar develops about 7 to 10 days later than the earlier coloring and maturing Arends Variety, U.S. Plant Pat. No. 2800 (a/k/a Paulared R). This new cultivar has been asexually reproduced on a variety of rootstocks and remains true to the description herein contained.

THE DRAWINGS

DETAILED DESCRIPTION

Flower

Figure 1:
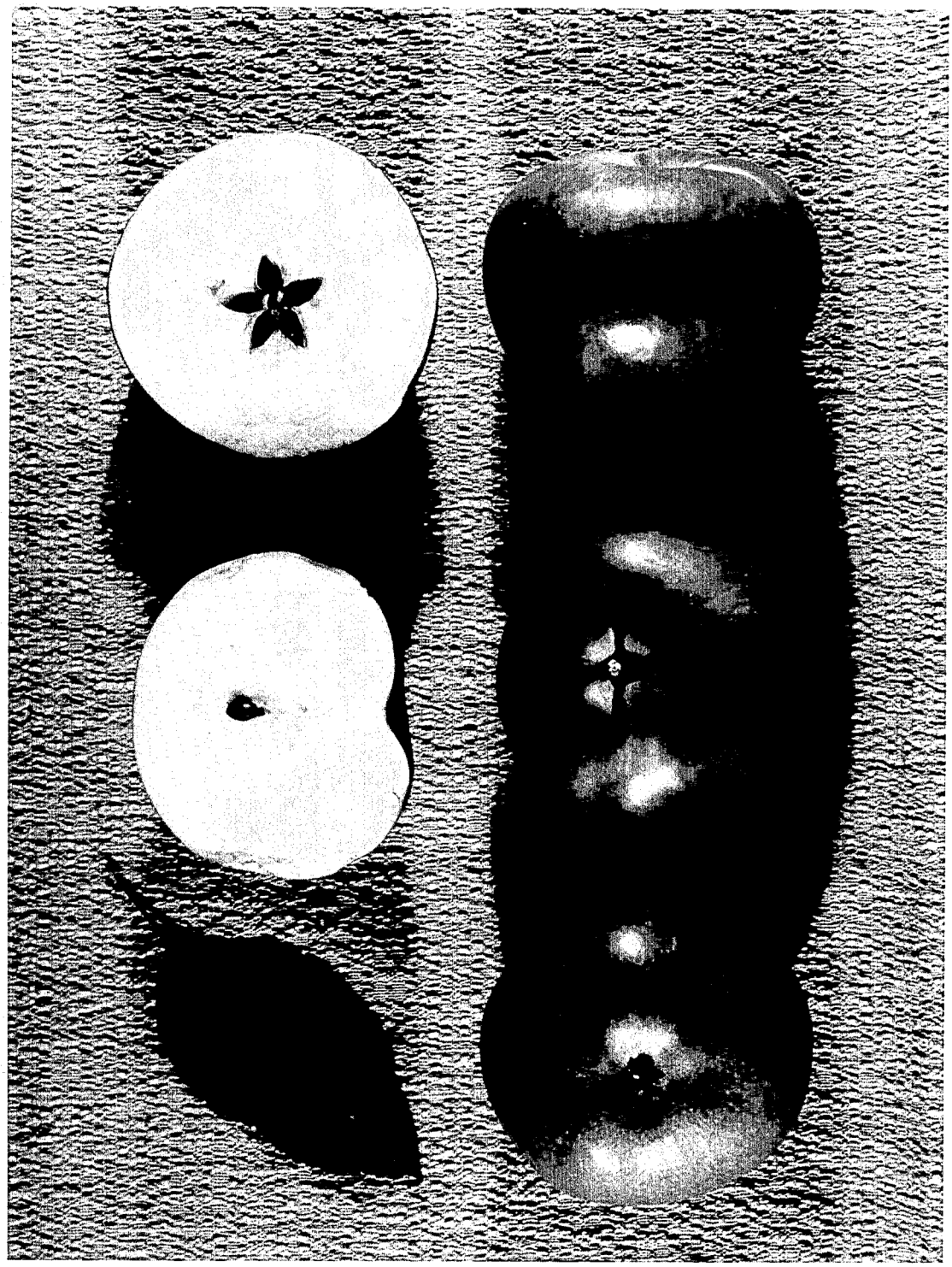
FIG. 1 is a color photograph which shows typical examples of the fruit and foliage of the Starling Cultivar. The following is a description of this new cultivar with the color designation according to the Horticultural Colour Chart issued by the British Colour Council in collaboration with The Royal Horticultural Society.
Figure 2:
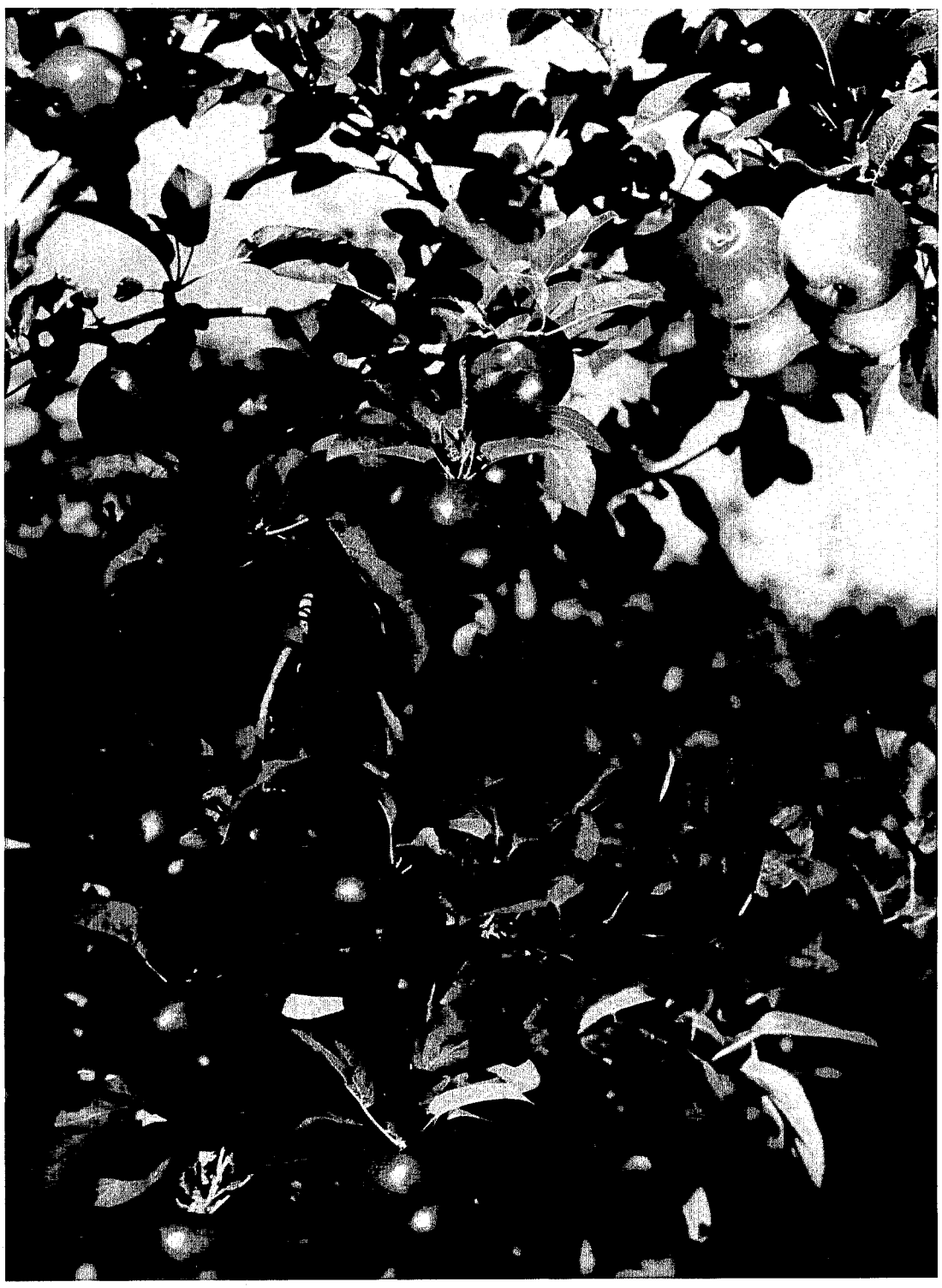
FIG. 2 is a Starling cultivar limb granted on a full tree of Macspur cultivar apple tree and shows the red color developing at least 7 days earlier than the Macspur cultivar fruit shown on the balance of the tree.

Pedicel: 1.5–2.0 cm ($\frac{1}{2}$–$\frac{3}{4}$ in.) in length.
Corolla: 2.4–3.5 cm (1.0–$1\frac{1}{2}$ in.) in diameter at anthesis.
Color: Rose Bengal from plate 25 in tight bud to b 25/3 with open flower.

Fruit

Size and shape: Globular to ovate. Axial diameter 5.2 to 5.8 cm (2.0 to $2\frac{1}{4}$ in.). Transverse diameter 7.0 to 8.5 cm ($2\frac{3}{4}$ to $3\frac{1}{4}$ in.).
Color: Overall blush red (Oxblood Red Plate 823/2) with slight stripping at calyx red.
Skin: Very smooth, waxy with small white sunken dots, skin thin, tough with no overall russeting.
Stem: Average 1.5 cm with $\frac{3}{4}$ of length extending above the shoulders, inserted vertically in the cavity.
Cavity: Obtuse, shallow, medium with smooth.
Basin: Shallow, wide, smooth.
Calyx: Persistent, closed, erect.
Calyx tybe: Urn shaped, closed.
Stamens: Marginal.
Core lines: Meeting.
Core: Distal, closed, medium sized, open.
Carpels: Cordate, smooth.
Seeds: Obtuse, non-tufted.
Flesh:
*Texture.*—Fine grained, crisp.
*Color.*—White.
*Quality.*—Excellent, subacid to bland.
*Aroma.*—Slight, pleasant.
Maturity season: 4–5 days before McIntosh and with MacSpur.
Keeping quality: Excellent, equivalent of McIntosh.
Use: Fresh eating, sauce, juice.

Tree

Growth habit: Non-Spur fruiting habit. Vigorous, spreading identical to McIntosh.
Leaves: Dark green, simple, ovate with accuminate tips and acute base, margins compound serrated, upper surface or leaves smooth with lower surface moderately pubescent.
Leaf size:
*Length.*—Width ratio 2:1.
Petiole: 2.0 to 2.5 cm in length, medium thickness, slightly pubescent.

We claim:

1. A new and distinct apple tree as shown and described herein.

* * * * *